US00PP31495P2

(12) United States Plant Patent
Pouillart

(10) Patent No.: US PP31,495 P2
(45) Date of Patent: Feb. 25, 2020

(54) ***LAVANDULA* PLANT NAMED 'LAVVAL'**

(50) Latin Name: *Lavandula angustifolia*
Varietal Denomination: Lavval

(71) Applicant: Valérie Pouillart, Glen (FR)

(72) Inventor: Valérie Pouillart, Glen (FR)

( * ) Notice: Subject to any disclaimer, the term of this patent is extended or adjusted under 35 U.S.C. 154(b) by 0 days.

(21) Appl. No.: 16/350,266

(22) Filed: Oct. 23, 2018

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — Penny J. Aguirre

(57) ABSTRACT

A new cultivar of *Lavandula* plant named 'Lavval' that is characterized by its f compact plant habit, its foliage that is grey-green in color, its flowers that are dark blue-purple in color, and its reblooming habit.

2 Drawing Sheets

Botanical classification: *Lavandula angustifolia.*
Variety denomination: 'Lavval'.

CROSS REFERENCE TO A RELATED APPLICATION

This application is related to a European plant breeders' rights application filed on Nov. 25, 2016, application No. 2016/2963. There have been no offers for sale anywhere in the world prior to the effective filing date of this Application and no accessibility to one of ordinary skill in the art could have been derived from the printed plant breeder's rights documents.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include a reference to the claimed plant on the website of plantipp.

BACKGROUND OF THE INVENTION

The present invention relates to a new and distinct cultivar of *Lavandula angustifolia* and will be referred to hereafter by its cultivar name, 'Lavval' 'Lavval' is a new variety of English lavender suitable for landscape and container use.

The new cultivar was discovered as a chance seedling by the Inventor in June of 2013 in the Inventor's garden in Gien, France. The parent plants are therfore unknown.

Asexual propagation of the new cultivar was first accomplished by the inventor by stem cuttings in March of 2017 in in Gien, France. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Lavval' as a unique cultivar of *Lavandula.*

1. 'Lavval' exhibits a compact plant habit.
2. 'Lavval' exhibits foliage that is grey-green in color.
3. 'Lavval' exhibits flowers that are dark blue-purple in color.
4. 'Lavval' exhibits a reblooming habit.

'Lavval' can also be compared to the *Lavandula angustifolia* cultivars 'Havana' (not patented), 'Thumbelina Leigh' (U.S. Plant Pat. No. 15,231) and 'Hidcote' (not patented). 'Havana' is similar to 'Lavval' in having dark blue-purple flowers. 'Havana' differs from 'Lavval' in having a less compact plant habit. 'Thumbelina Leigh' is similar to 'Lavval' in having a compact plant habit and in having a reblooming habit. 'Thumbelina Leigh' differs from 'Lavval' in having foliage that is bright green in color. 'Hidcote' is similar to 'Lavval' in having a compact plant habit. 'Hidcote' differs from 'Lavval' in lacking a reblooming habit.

BRIEF DESCRIPTION OF THE DRAWINGS

The accompanying colored photographs illustrate the overall appearance and distinct characteristics of one year-old plants of the new *Lavandula* as grown outdoors in 14-cm containers in 2018 in St. Thomas, Canada.

The photograph in FIG. 1 illustrates the plant habit of 'Lavval' in summer.

Figure 1:
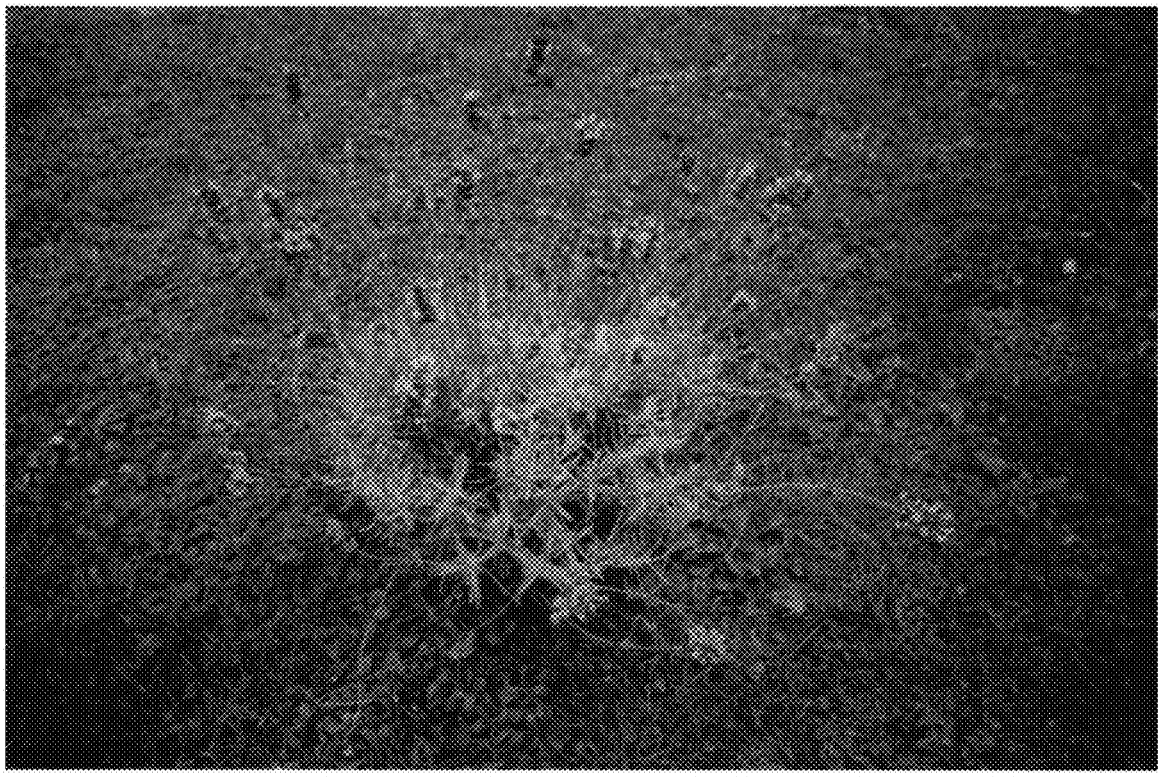
Figure 2:
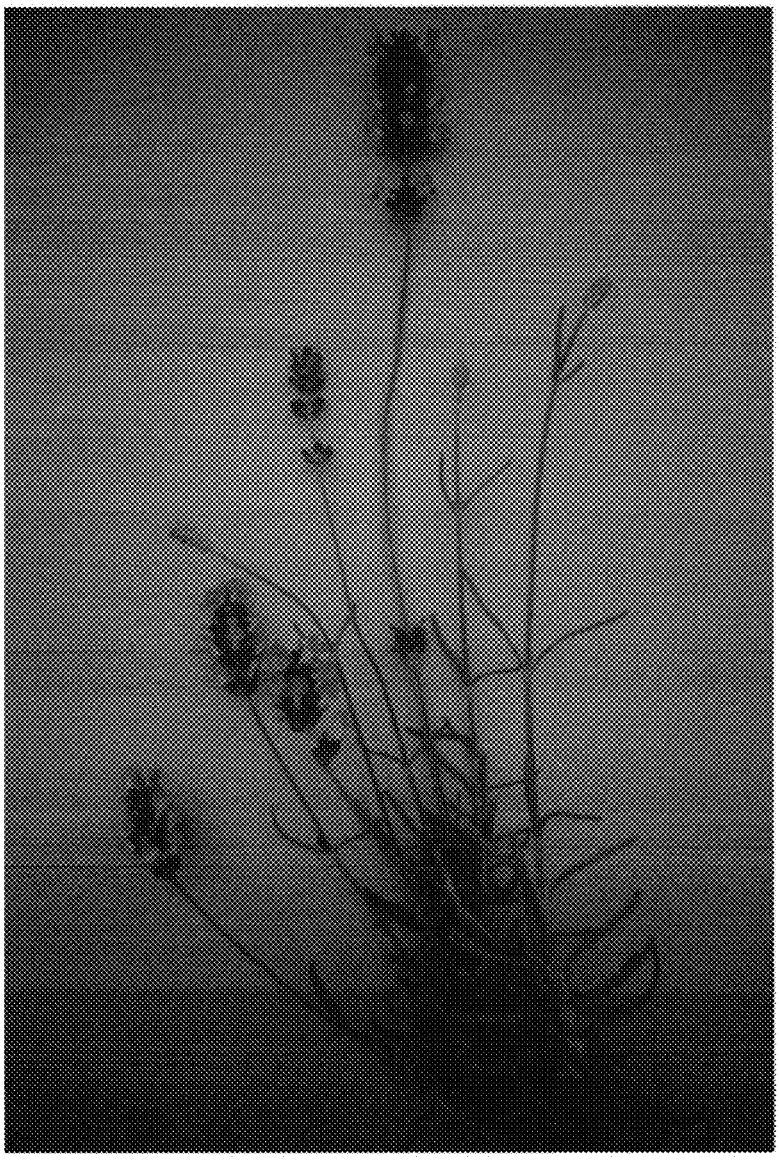

The photograph in FIG. 2 provides a close up view of an inflorescence of 'Lavval'.

The colors in the photographs are as close as possible with the digital photography techniques utilized and the color values cited in the detailed botanical description accurately describe the colors of the new *Lavandula*.

DETAILED BOTANICAL DESCRIPTION

The following is a detailed description of three year-old plants of the new cultivar as grown outdoors in 3-liter containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Reblooms from June to October in France.

*Plant type.*—Perennial, subshrub.

*Plant habit.*—Rounded foliage with flowering stems held above foliage, bushy.

*Height and spread.*—Reaches about 40 cm in height and spread in the landscape.

*Cold hardiness.*—At least in U.S.D.A. Zone 7b.

*Diseases and pests.*—No susceptibility or resistant to pests and diseases has been observed.

*Root description.*—Thin and fibrous, NN155D in color and changing to 165B as they age.

*Root development.*—Cutting root in 6 to 8 weeks and can be finished as a young rooted plant in 6 to 8 weeks from a rooted cutting.

*Propagation.*—Stem cuttings.

*Growth.*—Moderate to vigorous.

Stem description:

*Stem shape.*—Square.

*Stem color.*—Young; 144C and 161B, mature wood; 165C with strips of 165A.

*Stem surface.*—Moderately tomentose.

*Stem size.*—Main stem up to 25 cm in length and 3 cm in length, lateral stems up to 20 cm in length and 2 to 3 mm in diameter.

*Stem strength.*—Strong.

*Stem aspect.*—Held at 45° to 90° to vertical with the outer most flowering stems semi-erect in attitude.

*Branching.*—Up to 8 lateral stems per main stem.

*Internode length.*—4 mm to 2 cm.

Foliage description:

*Leaf shape.*—Narrowly elliptic to linear.

*Leaf division.*—Simple.

*Leaf base.*—Cuneate.

*Leaf apex.*—Obtuse-subacute.

*Leaf venation.*—Pinnate, color; NN137D on upper surface, 138C on lower surface, mid rib recessed on upper surface and raised on lower surface.

*Leaf margins.*—Entire and revolute.

*Leaf arrangement.*—Opposite.

*Leaf attachment.*—Sessile.

*Leaf number.*—Average of 26 per stem.

*Leaf surface.*—Upper surface; sparsely tomentose, lower surface; short tomentose with mid vein and margin tomentose.

*Leaf size.*—4 to 5 cm in length and 4 to 5 mm in width.

*Leaf color.*—Young upper surface; 137B, young lower surface; 137D, mature upper surface; 137A, mature lower surface; 138B.

*Leaf fragrance.*—Strongly fragrant, typical *Lavandula* scent.

Inflorescence description:

*Inflorescence type.*—Single spike to spikes with verticillasters (gaps between cymes).

*Inflorescence shape.*—Oblong/cylindrical, dense.

*Inflorescence number.*—1 Spike per flowering stem.

*Inflorescence fragrance.*—None.

*Spike whorls.*—Campanulate in shape, an average of 6 per spike, up to 1 cm in width and an average of 1.8 cm in width, color defined by petal and sepal colors.

*Lastingness of inflorescence.*—Average of 3 weeks with open flowers, flowers last an average of 2 days.

*Inflorescence size.*—4 to 5 cm in height and 1.8 cm in width.

*Inflorescence rachis.*—Up to 5 cm in length and 1.2 mm in width, 139C in color, densely tomentose surface.

*Flower buds.*—Average of 1.5 mm in length (above calyx) and 1.5 mm in diameter, oblong in shape, glabrous surface, 93C in color.

*Flowers.*—Outward aspect, self-cleaning, salviform in shape, persistant and turn 164B after maturity, up to 1 cm in length, 7 to 8 mm in diameter, tube; 7.5 mm in length and 1.3 mm in width, throat; 2 mm in diameter, number; up to 6 per cyme and up to 6 cymes per spike.

*Petals.*—1 upper lip with two lobes and 1 lower lip with three lobes, upper lip 4.5 mm in length and 4 mm in width, lower lip 3 mm in length and width, inner and outer surface when opening and mature 93C in color, throat color 92B to 92D, upper surface glabrous with long hairs at end of tube, lower surface smooth and glabrous.

*Calyx.*—5 elliptica sepals fused into a cylindrical tube with small tips at apex, 5 mm in length and 2 mm in width, inner surface glabrous but densely pubescent at apex (155A in color), outer surface densely pubescent (86A and 91D at base), color; inner surface 137C at base and 93B at apex, outer surface 86A with base 138C.

*Peduncles.*—Moderately strong, rounded square in shape held mostly upright, 4 to 15 cm in length and 1.7 to 2 mm in diameter, surface densely tomentose, 139C in color with dense tomentose hairs 157B in color.

*Pedicels.*—Moderately strong, round in shape, up to 1.4 cm in length and 0.8 mm in diameter, a blend of 91D and 138B in color, surface short villous, bracteoles present (infertile bracts); 1 to 2, lanceolate to filiform in shape, acuminate apex, truncate base, 8 mm in length, 3 mm in diameter, short villous surface, 165A in color on both surfaces.

*Flower bracts.*—Each cyme subtended by one bract, deltoid-broadly ovate in shape, acuminate apex, obtuse base, sessile, margin 1 undulation on each side, up 5 mm in length and 4.5 mm in width, upper surface glabrous with slightly tomentose mid-vein, lower surface glabrous, upper and lower surfaces 168D in color with veins 175A.

Reproductive organs:

*Pistils.*—1, pistil; 7 mm in length, stigma; bilobed, 86B in color, style; 6 mm in length, NN155C in color, ovary; 144D in color.

*Stamens.*—4, anthers; reniform, average of 0.5 mm in length, 161D in color with margin 161A, filament;

1.5 mm in length, filiform in shape, 155A in color, pollen; abundant in quantity, 17A in color.

*Seeds.*—1 to 3 per flower, 2.2 mm in length, 1.5 mm in width, oblong-subobovate in shape, 202A in color.

It is claimed:

1. A new and distinct cultivar of *Lavandula* plant named 'Lavval' as herein illustrated and described.

* * * * *